United States Patent
Zwiren et al.

(10) Patent No.: US 11,883,457 B1
(45) Date of Patent: Jan. 30, 2024

(54) METHOD OF ENHANCING COGNITION IN INDIVIDUALS WITH AT LEAST NORMAL COGNITION

(71) Applicant: OPTIGENEX INC., Scottsdale, AZ (US)

(72) Inventors: Daniel A Zwiren, Hoboken, NJ (US); O'neil Guthrie, Flagstaff, AZ (US); Vincent C Giampapa, Canadensis, PA (US)

(73) Assignee: OPTIGENEX INC.

( * ) Notice: Subject to any disclaimer, the term of this patent is extended or adjusted under 35 U.S.C. 154(b) by 0 days.

(21) Appl. No.: 17/903,284

(22) Filed: Sep. 6, 2022

(51) Int. Cl.
*A61K 36/74* (2006.01)
*A61P 25/28* (2006.01)
*A61K 9/00* (2006.01)
*A61K 9/70* (2006.01)

(52) U.S. Cl.
CPC .......... *A61K 36/74* (2013.01); *A61K 9/0053* (2013.01); *A61K 9/7023* (2013.01); *A61P 25/28* (2018.01)

(58) Field of Classification Search
None
See application file for complete search history.

(56) References Cited

U.S. PATENT DOCUMENTS

| | | |
|---|---|---|
| 6,264,994 B1 | 7/2001 | Castillo et al. |
| 6,346,280 B1 | 2/2002 | Castillo et al. |
| 6,607,758 B2 | 8/2003 | Castillo et al. |
| 6,797,286 B2 | 9/2004 | Bobrowski |
| 6,929,808 B2 | 8/2005 | Castillo et al. |
| 6,939,570 B1 | 9/2005 | Snow et al. |
| 7,029,710 B2 | 4/2006 | Castillo et al. |
| 7,285,293 B2 | 10/2007 | Castillo et al. |
| 7,314,642 B2 | 1/2008 | Castillo et al. |
| 7,754,250 B2 | 7/2010 | Castillo et al. |
| 8,115,031 B2 | 2/2012 | Yates et al. |
| 10,098,922 B1 * | 10/2018 | Giampapa ............ A61K 9/0053 |
| 2011/0097428 A1 | 4/2011 | Lake et al. |
| 2016/0250273 A1 | 9/2016 | Cam et al. |
| 2017/0333512 A1 | 11/2017 | Cam et al. |

OTHER PUBLICATIONS

Gampawar et al. (2022) Ageing Research Reviews 80: 101679. (Year: 2022).*
Harris et al. (2006) Neuroscience Letters 406: 260-264. (Year: 2006).*
Valdes et al. (2010) Neurobiology of Aging 31: 986-992. (Year: 2010).*
Zhan et al. (2018) Neurobiology of Aging 69: 111-116. (Year: 2018).*
Yu et al. (2018) Cortex 132: 29-40. (Year: 2018).*
C. Cosentino et al. and L. Torres, Reversible Worsening of Parkinson Disease Motor Symptoms After Oral Intake of Uncaria tomentosa, Clinical Neuropharmacology 31(5): 293-294.
Quinn et al., Phytochemicals in Alzheimer Disease: The Development of Clinical Trials, Pharmaceutical Biology 42 (supplement): 64-73.
Shi et al., Neuroprotective effects of aqueous extracts of Uncaria tomentosa: Insights from 6-OHDA induced cell damage and transgenic Caenorhabditis elegans model.
Castillo et al., Int'l Publication WO98/51302, Composition and Methods for Treating Alzheimer's Disease and Other Amyloidoses.
Mini-Mental State—A Practical Method for Grading the Cognitive State of Patients for the Clinician—Marshal F. Folstein, Susan E. Folstein and Paul R. McHugh.
Leukocyte Telomere Length is Unrelated to Cognitive Performance among Non-Demented and Demented Persons: An Examination of Long Life Family Study Participants—Ashrafi et al.
Cognitive performance and leukocyte telomere length in two narrow age-range cohorts: a population study—Mather et al.

* cited by examiner

*Primary Examiner* — Russell G Fiebig
(74) *Attorney, Agent, or Firm* — H. Jay Spiegel

(57) ABSTRACT

AC-11® is a federally registered trademark covering a product consisting of an aqueous extract of the botanical *Uncaria tomentosa*. Applicants have found that administration of AC-11® product in a pharmaceutically effective amount and for a sufficient time period results in enhancement of cognition in people with normal cognition prior to commencing administration. The method of administering the AC-11® product is disclosed and claimed.

14 Claims, 6 Drawing Sheets

METHOD OF ENHANCING COGNITION IN INDIVIDUALS WITH AT LEAST NORMAL COGNITION

BACKGROUND OF THE INVENTION

The present invention relates to a method of enhancing cognition in individuals with at least normal cognition. For almost 20 years, Applicants' Assignee Optigenex Inc. (Optigenex) has been refining, distributing, and selling products under the federally registered trademark AC-11® (Registration No. 2,930,140, registered Mar. 8, 2005, and claiming a date of first use of at least as early as Jul. 30, 2003). The products sold under the AC-11® trademark consist of an aqueous extract of the botanical *Uncaria tomentosa*. The AC-11® product is often sold as a vitamin supplement.

Optigenex found that application of the AC-11® product could result in lengthening of the telomeres in a cell. As such, on Nov. 30, 2017, Optigenex caused a U.S. patent application to be filed which was assigned Ser. No. 15/827,223. On Oct. 16, 2018, the application matured into U.S. Pat. No. 10,098,922, and corresponding International applications have either been granted or are currently pending.

Subsequently, Optigenex engaged in research to determine whether application of AC-11® in defined quantities and durations could be useful in promoting aspects of human health. During this process it was discovered, as explained in greater detail hereinafter, that such application of the extract of *Uncaria tomentosa* could result in enhanced cognition in individuals who, before receiving the product, had at least normal cognition. This patent application was filed to seek patent protection for this application of the AC-11® Uncaria tomentosa substance.

Subsequently, Optigenex conducted research to determine whether *Uncaria tomentosa* could be administered to people with positive results in health. After significant experimentation, Applicants discovered that for persons who were relatively healthy with normal cognition, administration of *Uncaria tomentosa* in prescribed doses resulted in enhanced cognition including statistically significant improvement in attention, memory, and executive function as well as improvement in social cognition. These results were attained by conducting a randomized double-blind cross-over placebo controlled pilot experiment. This experiment resulted in the conclusion that daily oral intake of a dose of *Uncaria tomentosa* resulted in statistically significant improvements in various aspects of cognition among relatively healthy patients with normal cognition prior to commencing the administration of *Uncaria tomentosa*. This invention differs from all prior art known to Applicants.

The following prior art is known to Applicants:

A number of U.S. patents are known to disclose use of various substances including administration of *Uncaria tomentosa* with the intent of treating Alzheimer's disease and/or other diseases related to amyloidosis. These patents are U.S. Pat. No. 6,264,994 to Castillo et al.; U.S. Pat. No. 6,346,280 to Castillo et al.; U.S. Pat. No. 6,607,758 to Castillo et al.; U.S. Pat. No. 6,797,286 to Bobrowski; U.S. Pat. No. 6,929,808 to Castillo et al.; U.S. Pat. No. 6,939,570 to Snow et al.; U.S. Pat. No. 7,029,710 to Castillo et al.; U.S. Pat. No. 7,285,293 to Castillo et al.; U.S. Pat. No. 7,314,642 to Castillo et al.; U.S. Pat. No. 7,754,250 to Castillo et al.; Published Application No. 2011/0097428 to Lake et al., and Published Application No. 2017/0333512 to Cam et al.

The present invention distinctly differs from the teachings of these patents and published applications because each of these prior art references presumes a cognitive decline such as is found in patients suffering from Alzheimer's disease. By contrast, a central feature of the present invention is that Applicants have found that administration of *Uncaria tomentosa* to people with normal health and cognition can enhance their cognition.

U.S. Pat. No. 8,115,031 to Yates et al. discloses the synthesis of quinic acid lactone which is a component of the hot water extract of *Uncaria tomentosa*. The patent discloses treatment of conditions of inflammation. It fails to teach enhancing cognitive function of initially normally cognitive people.

Published Application No. US 2016/0250273 to Cam et al. discloses blended preparations of *Uncaria tomentosa* extracts and oolong tea extracts to treat pathological plaques and tangles that accumulate in the aging brain in amyloidosis and taupathies. Again, as explained above, patients with amyloidosis and related conditions including Alzheimer's disease have reduced cognition and, as such, are not people who are known to be able to attain enhanced cognition from the inventive method.

A 2008 publication by C. Cosentino et al. and L. Torres (Reversible worsening of Parkinson disease motor symptoms after oral intake of *Uncaria tomentosa* (cat's claw). Clinical Neuropharmacology 31(5): 293-294.) discloses reversing worsening of Parkinson disease after oral intake of *Uncaria tomentosa*. The present invention distinguishes from this publication because the present invention relates to enhancing cognition in normally cognitive people.

A publication to Quinn et al. from 2004 (Phytochemicals in Alzheimer disease: The development of clinical trials. Pharmaceutical Biology 42 (supplement): 64-73) discloses attempts to utilize hydrophobic *Uncaria tomentosa* extracts to treat oxidative stress information, amnesia, tangles, and plaques in Alzheimer's disease. This publication fails to teach any improvement in cognitive function among people whose cognitive function is normal before the *Uncaria tomentosa* was administered.

A 2013 publication to Shi et al. (Neuroprotective effects of aqueous extracts of *Uncaria tomentosa*: Insights from 6-OHDA induced cell damage and transgenic *Caenorhabditis elegans* model. Neurochemistry International 62: 940-947) discloses neuro protective effects of aqueous extracts of *Uncaria tomentosa*. This publication fails to teach or suggest application of *Uncaria tomentosa* to enhance cognitive function of people with relatively normal cognitive function before the substance was administered.

International Publication WO98/51302 to Castillo et al. discloses compositions and methods for treating Alzheimer's disease and other amyloidosis. This reference fails to teach or suggest enhancing the cognition of people whose cognition is normal before administering a substance such as *Uncaria tomentosa*.

The references discussed above are representative of prior art efforts to treat mental decline including from dementia and Alzheimer's disease. What they all have in common is that they disclose potential treatments intended to reverse mental decline caused by disease exhibited in a person's brain cells and with varied results. In stark contrast to the prior art known to Applicants as exemplified hereinabove, in the present invention, the starting point for treatment is a person with tested normal cognition and application of the *Uncaria tomentosa* substance is intended to enhance cognitive function in such a person. This distinctly differs from the teachings of the prior art known to Applicants.

SUMMARY OF THE INVENTION

The present invention relates to a method of enhancing cognition in individuals with at least normal cognition. The present invention includes the following interrelated objects, aspects and features:

(1) In a first aspect, the present invention consists of Carboxy alkyl esters (CAEs) as the active ingredient of *Uncaria tomentosa* (UT) also known as uña gato or cat's claw, a multi-functional medicinal vine that has been used for over 2000 years including by ancient civilizations including that of the Tahuantinsuyo (Inca) empire. The bioactive components of UT are divided into hydrophobic and hydrophilic phytochemicals. The hydrophobic chemicals include uncarine F, speciophylline, mitraphylline, isomitraphylline, pteropodine, isopteropodine, etc. These hydrophobic chemicals are derived from tincture preparations (the use of alcohols to extract the chemicals from UT). The hydrophilic chemicals include CAEs, which are esters of quinic acid. These hydrophilic chemicals are derived from decoctions (the use of hot water to extract the chemicals from UT). The hydrophobic chemicals and the hydrophilic chemicals are structurally, chemically and functionally distinct/separate chemicals. Although both types of chemicals can be derived from the same vine (e.g., UT), research conclusions from one class of chemicals are not predictive of the other class of chemicals. For example, the hydrophobic chemicals can be toxic while the hydrophilic chemicals such as CAEs show no signs of toxicity at physiological dosages. The present invention is based on a specific class of hydrophilic chemicals called CAEs.

(2) CAEs are extracted and purified via known procedures to produce a specific article of manufacture. Briefly, the bark (~150 g) of UT is heated in water for 12-24 hours at 90-100° C. and the soluble extracts are decanted and ultra-filtered to remove components with a molecular weight that is greater than 10 kDa (e.g., tannins and flavanoids) while the remaining low molecular weight components are spray dried on maltodextrin. A variety of analytical methods have verified the CAE compositions derived from this procedure which produces up to 20% of CAEs per extract. Therefore, the present invention is based on UT derived from such a specific process that produces this specific composition of CAEs.

(3) CAEs have been found by Applicants to improve attention, memory, executive function and/or social cognition in cognitively healthy individuals. A randomized double-blind cross-over placebo controlled human experiment conducted by Applicants, as described in greater detail hereinafter, showed that daily (30 days) oral intake of AC-11® pills, the trademark covering an *Uncaria tomentosa* substance, improves cognitive functions among relatively healthy individuals with normal cognition initially. This statistically significant improvement occurred as early as one month after AC-11® intake and could be sustained out to three months. Therefore, the present invention teaches cognitive improvement among relatively healthy individuals with normal cognition. A key point is that the present invention is focused on healthy individuals with normal cognition as opposed to disease states (Alzheimer's disease, Parkinson's disease, inflammatory disease, etc.) or pathological preparations (in vitro or in vivo plaques, tangles, etc.).

(4) The key distinction between the present invention and prior art known to Applicants is the fact that the present invention has been found to be an effective treatment to enhance cognition among people whose cognition is, generally speaking, normal. In the art of determining cognition, a mini-mental state examination (MMSE) is a widely used tool for assessing orientation in time, orientation to place, immediate memory recall, dyscalcula, attention, delayed memory, language repetition, language 3-stage commands, reading skills, and motor functions. A person is examined using this test and the results of the test are transformed into a numerical score. A score of ≤20 indicates less than normal cognition. A score greater than 20 indicates at least normal cognition. In determining whether the present invention is actually an effective means for enhancing cognition, subjects who were tested were all found to have an MMSE score greater than 20, and in all cases 30. The MMSE test employed in the above-mentioned experiment was the Folstein Mini-Mental State examination as reported in the Journal of Psychiatry, J. Psychiat, Res. 1974, Vol. 12, pp. 189-198, © 1975 Pergamon Press. In that test, a score greater than 20 evidences normal cognition. The maximum score when testing for one type of cognition such as "attention" is 30. Where multiple types of cognition are being tested, such as "attention" and "calculation," the maximum attainable score is 35. In the test, each subject was tested for multiple types of cognition and each subject attained a score 30.

(5) In determining whether the present invention actually succeeds in improving cognition of normally cognitive individuals, Applicants conducted a randomized double-blind cross-over placebo controlled pilot experiment which is a procedure known to scientists to facilitate credible determining of whether some scientific result is merely random or, instead, is reproducible and provable.

(6) The study was conducted in which 18 individuals were found to have an MMSE score greater than 20. In fact, each of the participants in the study had an MMSE score ≥30 meaning that each participant in the study was already mentally functioning at a high cognitive level.

(7) At the conclusion of the study, each participant was tested again and the results revealed that daily oral intake of *Uncaria tomentosa* in the form of pills sold under the trademark AC-11® resulted in statistically significant improvement in attention, memory, and executive function. The majority of participants also evidenced improvement in social cognition. Improvement in attention was most resilient and persistent. Accordingly, Applicants properly concluded that the present invention actually achieves results worthy of patent protection.

As such, it is a first object of the present invention to provide a method of enhancing cognition in individuals with at least normal cognition.

It is a further object of the present invention to provide such an invention in which *Uncaria tomentosa* (UT) is administered to individuals of normal cognition to enhance their cognition.

It is a still further object of the present invention to provide such a method in which a randomized double-blind cross-over placebo controlled pilot experiment demonstrated the efficacy of the present invention.

It is a yet further object of the present invention to provide such a method in which improvements result in attention, memory, executive function, and social cognition.

These and other objects, aspects and features of the present invention will be better understood from the following detailed description of the preferred embodiment when read in conjunction with the appended drawing figures.

SPECIFIC DESCRIPTION OF THE PREFERRED EMBODIMENT

Figure 1:
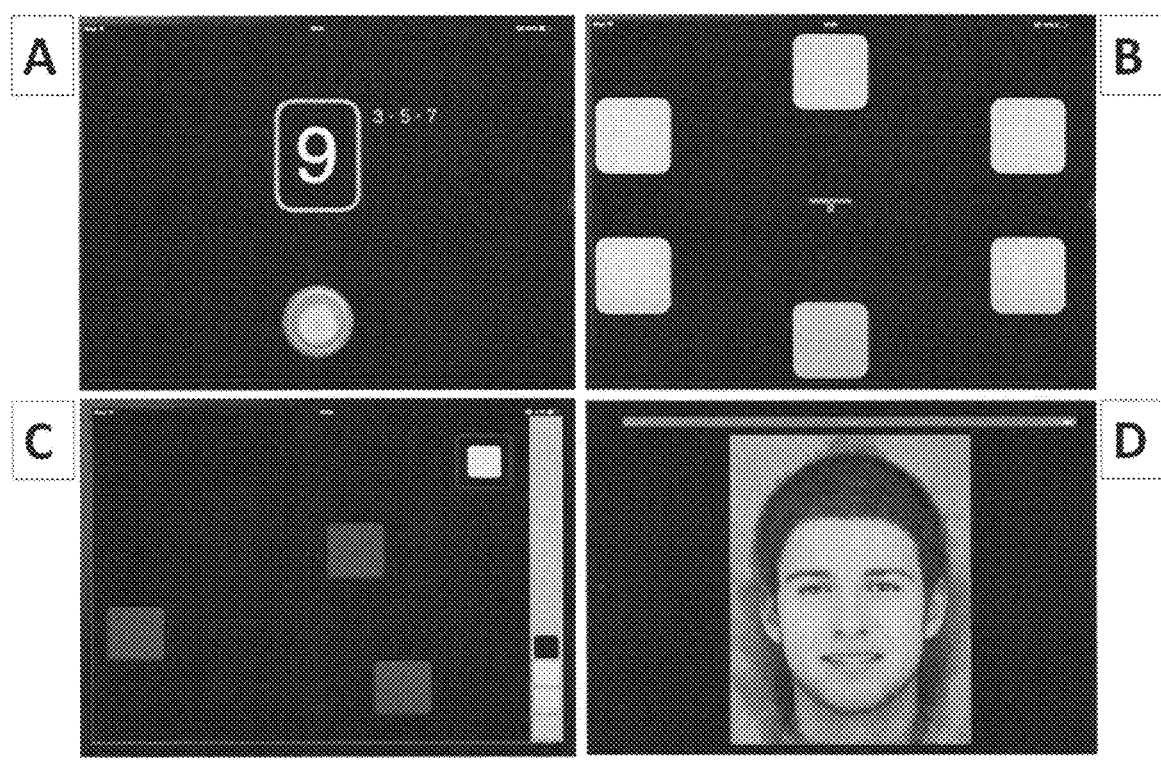
FIG. 1 shows computer screen shots of the neuropsychological assessments employed in studying the present invention.

AC-11® is a widely used commercially available dietary supplement including as an active ingredient *Uncaria tomentosa*. Those who have taken AC-11® have exhibited health benefits that include, improved DNA repair, lengthened telomeres, reduced inflammation and increased bioavailability of aromatic amino acids. To date, the role of AC-11® on neuropsychological functions has been unresolved. The present invention involves testing the hypothesis that daily oral intake of AC-11® will improve neuropsychological functions for people with normal cognitive function.

To test this hypothesis, a randomized double-blind crossover placebo controlled pilot experiment was conducted.

Standardized unsupervised neuropsychological assessments served as the main methodology. These assessments included individual tests that measure attention, memory, executive function, and social cognition. A total of 18 individuals participated in the study and each individual was relatively healthy with normal cognition at baseline.

The results of the study revealed that daily oral intake of AC-11® resulted in statistically significant (t=2.4, p<0.05) improvement in attention, memory, and executive function. Additionally, 64% of the participants evidenced improvement in social cognition. Improvement in attention was the most resilient and persistent. As such, Applicants have concluded that healthy individuals with normal cognition may use AC-11® to provide a "cognitive boost" as desired and when needed.

Cognition is a nebulous construct. However, one reasonable conception of cognition is the coordinated response of multiple brain regions in order to execute a particular function. Such functions can range from the detection of a stimulus to complex behavioral and emotional tasks. Throughout history, healthy individuals have sought to improve their cognition to provide a competitive advantage in educational, occupational, recreational and social endeavors. For instance, university students in the United States have often misused prescription stimulants to improve their cognition for educational gains.

Among a wider demographic, up to 62% of individuals have misused prescription drugs to enhance cognition (Maher, 2008). Survey data suggest that one in five respondents may consume drugs to improve their cognitive performance (Maher, 2008). There appears to be a need/desire among the general population to increase cognitive functions when needed (before taking an exam, completing a work-related task, etc.). However, the misuse of prescription drugs to achieve cognitive improvement can be illegal and risky due to the development of side effects such as psychosis, insomnia and irritability (Nicholson and Wilson, 2017: Wozniak-Karczewska et al., 2018). Furthermore, it is unknown whether misused prescription drugs can actually improve cognition among healthy individuals who already have normal cognition. Therefore, the perception of cognitive enhancement from the misuse of prescription drugs might be dubious at best.

The perception of cognitive enhancement can be achieved in at least three ways. One is the placebo effect, where the act of taking a drug with presumed benefits, can lead to positive cognitive outcomes when in fact the drug imbues no real effect on cognition. A second is the self-appraisal effect, where the drug alters one's perception of a given task (e.g., the amount of work to be done and the quality of the work) without improving cognitive performance of the task (Hurst et al., 1967). A third is the arousal effect, where the drug potentiates energy, wakefulness or motivation which increases task performance yet cognition remains unchanged. Due to these confounding variables, randomized double-blind placebo-controlled experiments that employ quantitative measures of cognition are needed to demonstrate whether the present invention is actually effective to enhance cognition. Therefore, the study was designed to determine whether AC-11® could increase cognitive performance among relatively healthy individuals with normal cognition.

Participants in the study were recruited for the study via digital and print announcements in Northern Arizona USA. These announcements directed prospective participants to make an appointment for an initial intake interview. Prior to this initial interview each subject was randomly assigned to a drug-then-placebo (DP) group or a placebo-then-drug (PD) group (drug=AC-11®). During the initial interview, the subjects were screened for cognitive deficiency by taking and passing the mini-mental status examination (MMSE) (Folstein et al., 1975). The MMSE is a widely used (e.g., doctor's office, hospitals or clinical settings) tool for assessing orientation in time, orientation to place, immediate recall (memory), dyscalculia, attention, delayed verbal recall (delayed memory), language repetition, language 3-stage commands, reading, and motor functions. A score ≤20 indicates less than ideal cognition. Each participant in the current study exhibited extremely high scores of ≥30 based upon testing for multiple types of cognition, an indication that each participant was already functioning at high cognitive levels.

Each participant was also queried to ascertain general health and neurologic status. They were all asked whether they believed their cognition to be normal. All answered in the affirmative. All participants presented with relatively normal health and no neurologic deficiencies. Additionally, participants were probed for eligibility for the study and basic demographic data (sex, age, educational level, etc.) were collected from each participant. A total of 18 healthy individuals with high cognitive status completed the entire study. Both adult females (N=11) and males (N=7) participated in the study. The participants ranged in age from 19 to 66 years old. They exhibited a range of educational achievements from high school to doctoral degrees. These participants self-identified as Caucasian, Asian, and Hispanic. All participants submitted informed written consent to participate in the study and the study received institutional review board (IRB) approval and oversight.

Neuropsychological assessments. For the study, neurocognitive functions were evaluated with unsupervised computer automated assessments from the Cambridge Neuropsychological Test Automated Battery (CANTAB). CANTAB is published in over 2,000 peer reviewed articles and is widely used in clinical, academic and pharmacologic research (Backx et al., 2020; Barnett et al., 2016; Wild et al., 2008). The CANTAB assessments are fully automated (from testing to scoring and data tabulations) with visual on-screen and auditory voice-over guidance from training to final assessments.

Each assessment began with a training paradigm to get participants familiar with the intended tasks. Once a given participant is fully trained, then the assessment commences. The training, assessments and the transition between them (and between assessments) are all unsupervised and artificial intelligence (AI) driven to remove bias induced by the interference of study staff (researchers). A total of four neuropsychological assessments (rapid visual information processing; paired associate learning; spatial working memory; and emotional bias task) were pursued in the study. Each assessment was designed to limit learning effects, therefore each assessment can be administered to the same participants over time (Backx et al., 2020). For instance, for each test session, test stimuli were presented at random from a large pool of stimuli or alternate test stimuli were selected which limits the possibility that a given participant will complete the same stimulus induced task more than once. This adaptive paradigm ensured little or no practice effects from taking the same assessment multiple times. FIG. 1 provides instantaneous screen shots of an exemplary assessment.

Rapid Visual Information Processing (RVP). This assessment evaluated sustained attention (Backx et al., 2020; Sahakian et al., (1989). At a rate of 100 digits per minute, 1 to 9 digits were presented successively in pseudorandom order. Participants were tasked with motor responses to target sequences, such as three consecutive odd or three even digits (3-5-7, 2-4-6, 4-6-8, etc.) as quickly as possible. Stimulus duration was 600 millisecond (ms) with no inter-stimulus intervals. Target sequences may be one or multiple simultaneous sequences. Outcomes measured included the mean latency (in ms) of responses to targets.

Paired Associate Learning (PAL). This assessment evaluated visual episodic memory (Barnett et al., 2016). A number of boxes were displayed and for some boxes their unique patterns (contents) randomly appeared then disappeared briefly. A given pattern (content within a specific box) was then presented in the middle of the computer screen and the participant was tasked with remembering which of the original set of boxes contained the pattern and where the box was localized. The difficulty of this task increased with each successful trial. Outcomes measured included errors in task completion (memory errors).

Spatial Working Memory Assessment (SWM). This assessment evaluated executive function via retention and manipulation of visuospatial information (Owen et al., 1990; Rabbitt and Lowe, 2000). The test involved the presentation of a number of colored squares (boxes). Participants were tasked with selecting the boxes and using a process of elimination, the participants found one yellow 'token' in each of a number of boxes and used them to fill up an empty column on the right-hand side of the computer screen. The number of boxes were gradually increased until a maximum of 12 boxes were shown for the participant to search. The color and position of the boxes used were changed from trial to trial to discourage the use of stereotyped search strategies. Outcomes measured included errors in selecting boxes that were already found to be empty and revisiting boxes which were already found to contain a token (executive function errors).

Emotional Bias Task (EBT). This assessment evaluated social cognition via detection of perceptual biases in facial emotions, using images of faces displaying magnitudes between happy and disgust emotions (Kelaiditis et al., 2021; Tristao et al., 2022). Faces were presented at a rate of 150 ms, followed by a two-alternative forced choice where participants were required to select one of the two emotions. Outcome measures included the percentage of bias toward happy or disgust emotions.

Experimental Research Design. The study employed in accordance with the teachings of the present invention deployed a randomized double-blind placebo cross-over research design. Participants were randomized to one of two groups (DP or PD) before the initial intake interview. No attempt was made to equalize the number of participants in each group, therefore random allocation resulted in 11 participants in the DP group and seven participants in the PD group. The DP group started the study by taking the neuropsychological assessments at baseline then they consumed AC-11® for 1-month. AC-11® consumption included oral intake of one 350 mg capsule twice daily (total of 700 mg/day) for 30 days. At the end of this 30 day period, participants took neuropsychological assessments again in order to determine whether AC-11® induced an improvement in scores from baseline.

These same participants then experienced a washout period, in which they did not take AC-11® or a placebo for 1-month. At the end of this washout period, the same participants took the neuropsychological assessments again. They then consumed the placebo (350 mg capsule twice daily, total of 700 mg/day) for 1-month and at the end of this month they took the neuropsychological assessments for the final time. This particular experimental research design allowed for within-group comparisons. For instance, within the same group of subjects, one can determine whether AC-11® had an effect on cognitive function and one can determine whether or not the placebo had similar or no effects. Therefore, the research question pursued in the study could be answered with this cross-over design on the DP group. However, to further interrogate the research question the PD group was also investigated.

The PD group started the study by taking the neuropsychological assessments at baseline then they consumed placebo for 1-month. At the end of this month, they took the neuropsychological assessments again in order to determine whether the placebo had any positive effects relative to baseline. These same participants then experienced a washout period, where they did not take placebo or AC-11® for 1-month. At the end of this washout period, the same participants took the neuropsychological assessments again. They then consumed AC-11® for 1-month and at the end of this month they took the neuropsychological assessments for the final time.

This particular experimental research design allowed for within-group comparisons. Therefore, one can determine whether placebo or AC-11® had an effect on cognitive function with just the PD group. Combining the two cross-over designs (that of the DP and PD groups) provided a rigorous, confirmative and powerful experimental approach for determining and evaluating efficacy of AC-11® in cognitive improvements.

Additionally, all study staff (researchers) were blinded to the scoring of each neuropsychological assessment and tabulation of test results from each participant. Unblinding occurred after test scoring and data tabulations. Similarly, each participant was blinded to whether they were consuming AC-11® or the placebo. The AC-11® and placebo capsules were identical in appearance. The AC-11® capsules contained carboxy alkyl esters (CAE; active ingredient) and Manioc Maltodextrin (starch). The placebo capsules were composed of Manioc Maltodextrin. The capsule materials were composed of titanium dioxide (food coloring).

Statistical Analysis. The aim of the current study was to determine whether AC-11® can improve cognitive functions among individuals with normal cognition functions. Statistical comparisons between baseline cognitive functions and cognitive functions after AC-11® consumption provided data to directly address this aim. Therefore, paired-samples t-tests were deployed to detect statistically significant differences relative to baseline. Two experimental groups (DP and PD) were deployed and each group served as its own within-group control, therefore, the specific aim could be evaluated with anyone of the groups (DP or PD). A p-value of <0.05 was used as the significance criterion. A professional graphing and statistical software suite (GraphPad Software, Inc., La Jolla, CA. USA) was deployed for all graphing and statistical computations.

Results. The purpose of the current study was to determine whether or not daily oral intake of AC-11® would improve cognitive functions among relatively heathy individuals with normal cognition. Therefore, the results from cognitive assessments after daily oral intake of AC-11® was compared to the results from cognitive assessments at baseline (at the start of the study). If AC-11® treatment resulted in cognitive test results that were better than the test results at baseline then this was interpreted as AC-11® having induced improvement in a particular cognitive function. To increase the rigor of the experimental research design and to further qualify interpretations of the results, a placebo treatment condition was also included. Therefore, the results from cognitive assessments after daily oral intake of the placebo was compared to the results from cognitive assessments at baseline (at the start of the study). Four cognitive domains were assessed in the current study and they included, attention, memory, executive function and social cognition. FIG. 1 shows computer screenshots of the neuropsychological assessments deployed in the current study: (A) Attention: rapid visual information processing; (B) Memory: paired associate learning; (C) Executive function: spatial working memory; and (D) Social cognition: emotional bias task.

Figure 2:
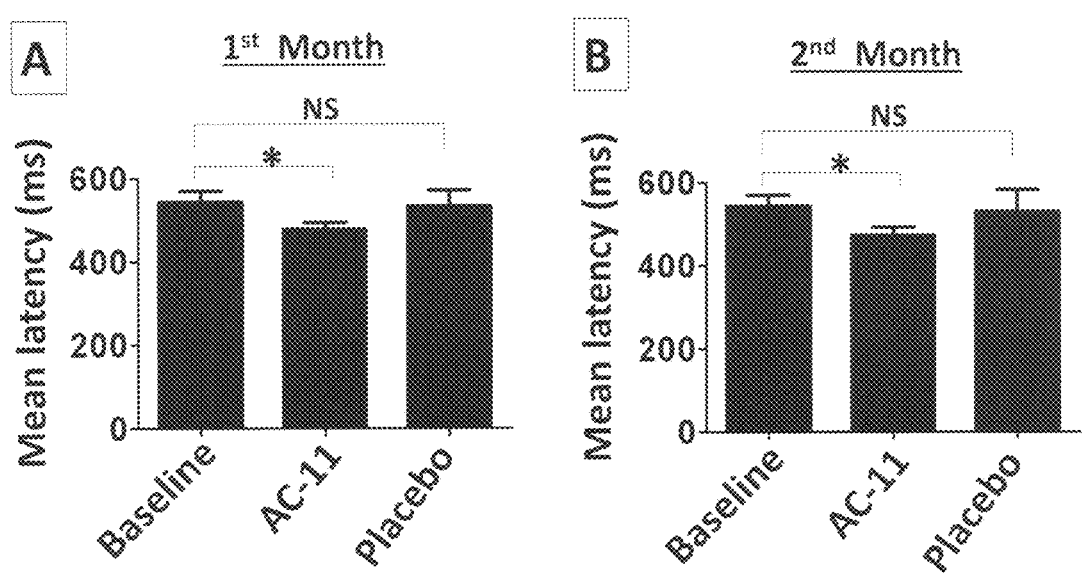
FIG. 2 shows bar graphs demonstrating improved attention through application of the present invention.

Attention: FIG. 2 reveals that oral intake of AC-11® improved attention above baseline (beginning of the study) levels. Furthermore, this improvement was maintained for two months (second month of the study). FIG. 2A reveals baseline attention scores, as well as attention score after 1-month oral intake of AC-11® and 1-month intake of placebo. The group who consumed AC-11® showed an improvement in attention compared to baseline while the group who consumed the placebo showed no improvement. This suggest that 1-month oral intake of AC-11® was sufficient to improve attention among normal/healthy individuals. FIG. 2B shows that this positive AC-11® effect was persistent out to two months (1-month after cessation of AC-11®). Therefore, AC-11® intake enhanced attention and this enhancement was consistent across two months.

As shown in FIG. 2: Administration of AC-11® resulted in improved attention within one month. Panel A shows that after one month of daily oral intake of AC-11® there was a statistically significant improvement in mean latency (lower scores equal better performance) compared to baseline (at the beginning of the study). Note that one month of oral intake of the placebo resulted in no statistically significant improvement compared to baseline. Panel B shows that the statistically significant improvement in attention that was induced by AC-11® was stable for a second month (one month after cessation of AC-11®). Note that the placebo continued to have no effect. Bars=mean±S.E.; ms=millisecond; NS=not statistically significant; *=p<0.05 or statistically significant.

Statistical computations were conducted and the results confirmed the conclusion that AC-11® improved "attention." Comparing baseline attention scores to attention scores after 1-month (1-month into the study) of AC-11® intake resulted in statistically significant improvement (t[10]=2.376, p=0.0389; two-tailed). One month after AC-11® cessation (2-months into the study), this statistically significant effect was still maintained (t[9]=20.388, p=0.0407; two-tailed). However, comparing baseline attention scores to attention scores after 1-month (1-month into the study) placebo intake resulted in no statistically significant improvement (t[6]=0.9216, p=0.3926; two-tailed). One month after placebo cessation (2-months into the study), there was still no statistically significant placebo effect (t[5]=1.563, p=0.1787; two-tailed). Therefore, only the AC-11® treatment improved attention.

Figure 3:
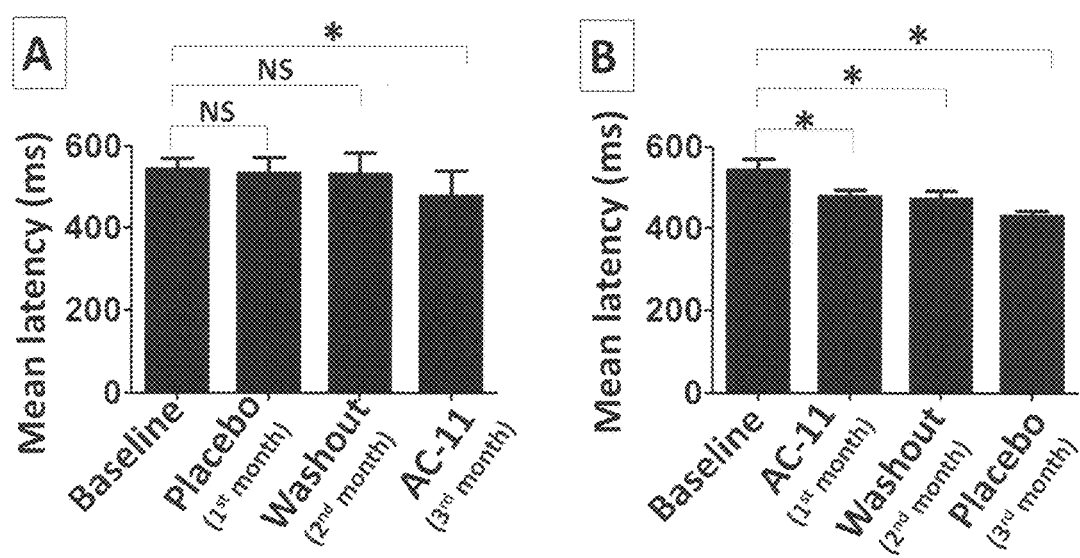
FIG. 3 shows bar graphs demonstrating that late stage oral intake of *Uncaria tomentosa* resulted in improved attention.

FIG. 3 reveals additional data that confirmed the positive effect of AC-11® on attention. FIG. 3A shows the results for a group of participants who received placebo the first month of the study and their attention scores were similar to their scores at baseline. This indicates that a placebo had no effect on attention. These same participants then went through a month long washout period (break or rest period). After this washout period their scores did not change and remained the same as that at baseline. However, when AC-11® was introduced and the same participants consumed AC-11® for 1-month, there was a significant improvement in their attention scores compared to baseline scores. This suggest that the introduction of AC-11® to the placebo group resulted in the improvement of their attention scores.

FIG. 3B further confirms this conclusion by showing the results for a group of participants who received AC-11® the first month of the study and their attention scores were improved relative to their scores at baseline. This indicates that AC-11® had a positive effect on attention. These same participants then went through a month long washout period (break or rest period). After this washout period their scores remained improved relative to baseline. Interestingly, when placebo was introduced and the same participants consumed the placebo for 1-month, there scores continued to be better than that at baseline. This further confirmed that the introduction of AC-11® improved attention and this improvement may last months after cessation of AC-11® intake.

Explanation of FIG. 3: Late-stage oral intake of AC-11® improved attention. Panel A shows the participants who experienced daily ($1^{st}$ month) oral intake of the placebo, then they experienced 30 days of no treatment (washout period: $2^{nd}$ month) and lastly, these same participants took AC-11® for 30 days ($3^{rd}$ month). Note that the only statistically significant improvement in attention occurred at 3 months due to AC-11® treatment (lower scores equal better performance). Panel B shows the participants who experienced daily ($1^{st}$ month) oral intake of AC-11®, then they experienced 30 days of no treatment (washout period: $2^{nd}$ month) and lastly, these same participants took the placebo for 30 days ($3^{rd}$ month). Note that AC-11® treatment improved attention after one month of treatment and this improvement continued out to 3 months. Furthermore, placebo intake did not prevent this positive effect of time. Bars=mean±S.E.; ms=milliseconds; NS=not statistically significant; *=p<0.05 or statistically significant.

Statistical computations were conducted on the data in FIG. 3. There was no statistically significant (t[6]=0.9216, p=0.3923; two-tailed) difference between baseline attention scores and attention scores following placebo treatment. Similarly, there was no statistically significant difference (t[5]=1.563, p=0.1787; two-tailed) between baseline attention scores and attention scores following the washout period. However, there was a statistically significant difference (t[8]=3.468, p=0.0085; two-tailed) between baseline attention scores and attention scores following AC-11® intake. This demonstrates that AC-11® was successful at improving attention among the group of participants who consumed the placebo first then AC-11® second.

Interestingly, administration of AC-11® was also successful at improving attention among the group of participants who consumed AC-11® first then placebo second. For instance, there was a statistically significant (t[10]=2.376, p=0.0389; two-tailed) difference between baseline attention scores and attention scores following AC-11® intake. Similarly, there was a statistically significant difference (t[9]=2.388, p=0.0407; two-tailed) between baseline attention scores and attention scores following the washout period. Lastly, there was a statistically significant difference (t[8]=3.468, p=0.0085; two-tailed) between baseline attention scores and attention scores following placebo intake. Therefore, the AC-11® induced improvement in attention was sustained beyond the washout period and even after placebo intake.

Figure 4:
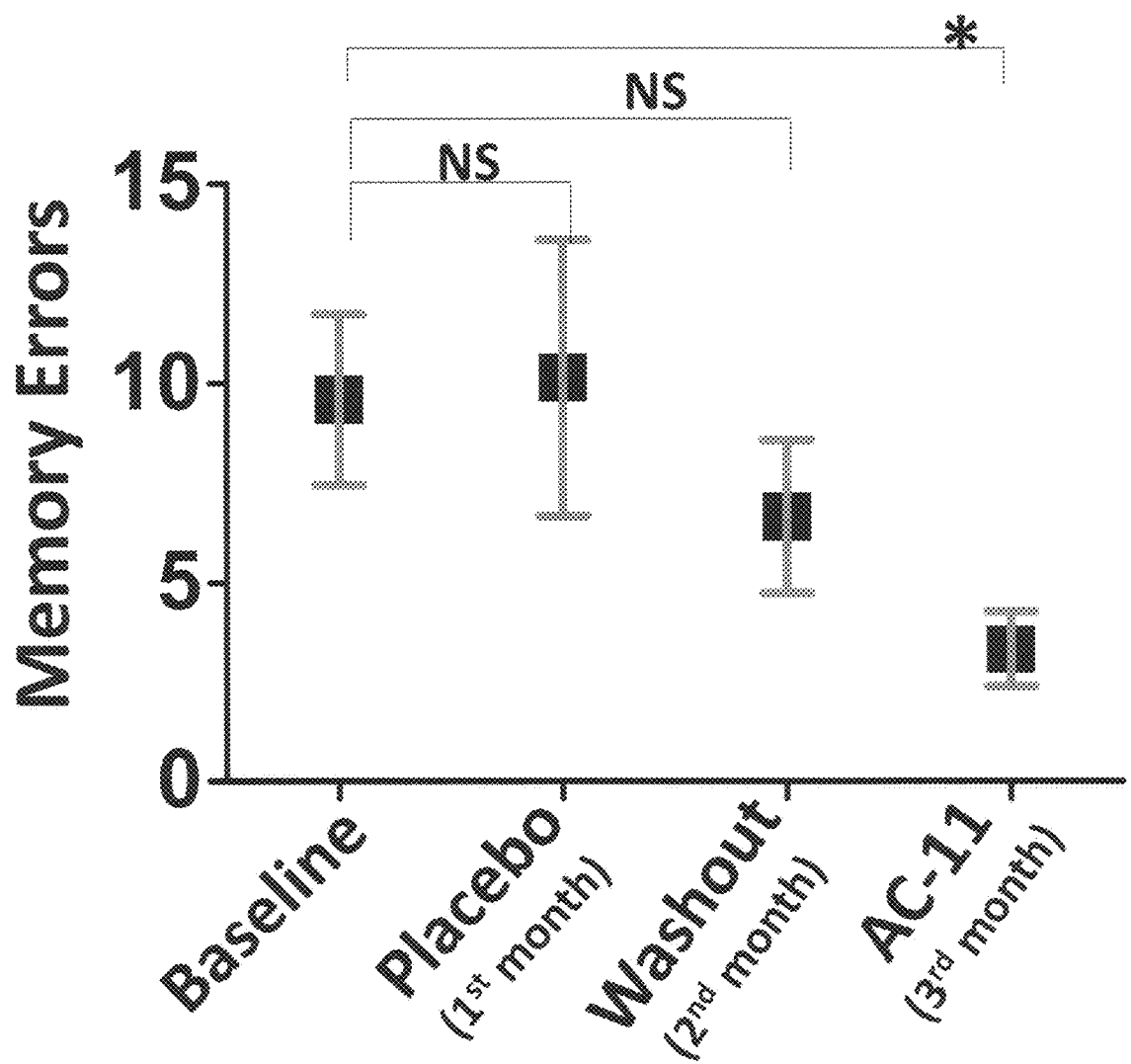
FIG. 4 shows a graph demonstrating that application of the present invention results in improved memory.

Memory: FIG. 4 reveals that daily oral intake of AC-11® improves memory. The group of participants who were treated with placebo evidenced no improvement in memory compared to their baseline memory scores. This demonstrates that placebo intake did not increase or decrease their memory performance. Interestingly, these same participants showed improvement in memory after the 1-month washout period. It is unknown why the participants would exhibit improvement in memory at this stage of the study since the washout period is a period where they refrained from both placebo and AC-11® intake. When these same participants consumed AC-11® their memory scores continued to improve. This suggest that AC-11® intake does not impede improvements in memory and contributes to better memory.

FIG. 4: Oral intake of AC-11® improved memory. This figure shows quantification of memory errors for participants at baseline (the beginning of the study). These participants first experienced 1-month of placebo by oral intake. Note that their memory errors did not improve after 1-month of placebo intake. Next, the participants experienced a 1-month washout period (rest period). Their memory errors were reduced but still not statistically different from baseline. Lastly, the participants experienced 1-month of oral intake of AC-11®. Note that their memory errors now showed a statistically significant improvement (lowest scores) compared to their scores at baseline. Boxes=mean±S.E.; NS=not statistically significant; *=p<0.05 or statistically significant.

Statistical computations revealed that there were no significant differences between memory scores at baseline and memory scores after placebo intake (t[6]=0.7101, p=0.5043; two-tailed). This is an indication that the placebo had no effect on memory. Additionally, there was no statistically significant difference (t[5]=1.736, p=0.1431; two-tailed) between memory scores at baseline and memory scores after 1-month of washout. This means that although memory scores showed some level of improvement, this effect was not significantly different from chance. However, statistical computations revealed that there was a significant difference (t[5]=2.951, p=0.0318; two-tailed) between memory scores at baseline and memory scores after AC-11® intake. This means that the AC-11® induced improvement in memory scores was not due to chance.

Figure 5:
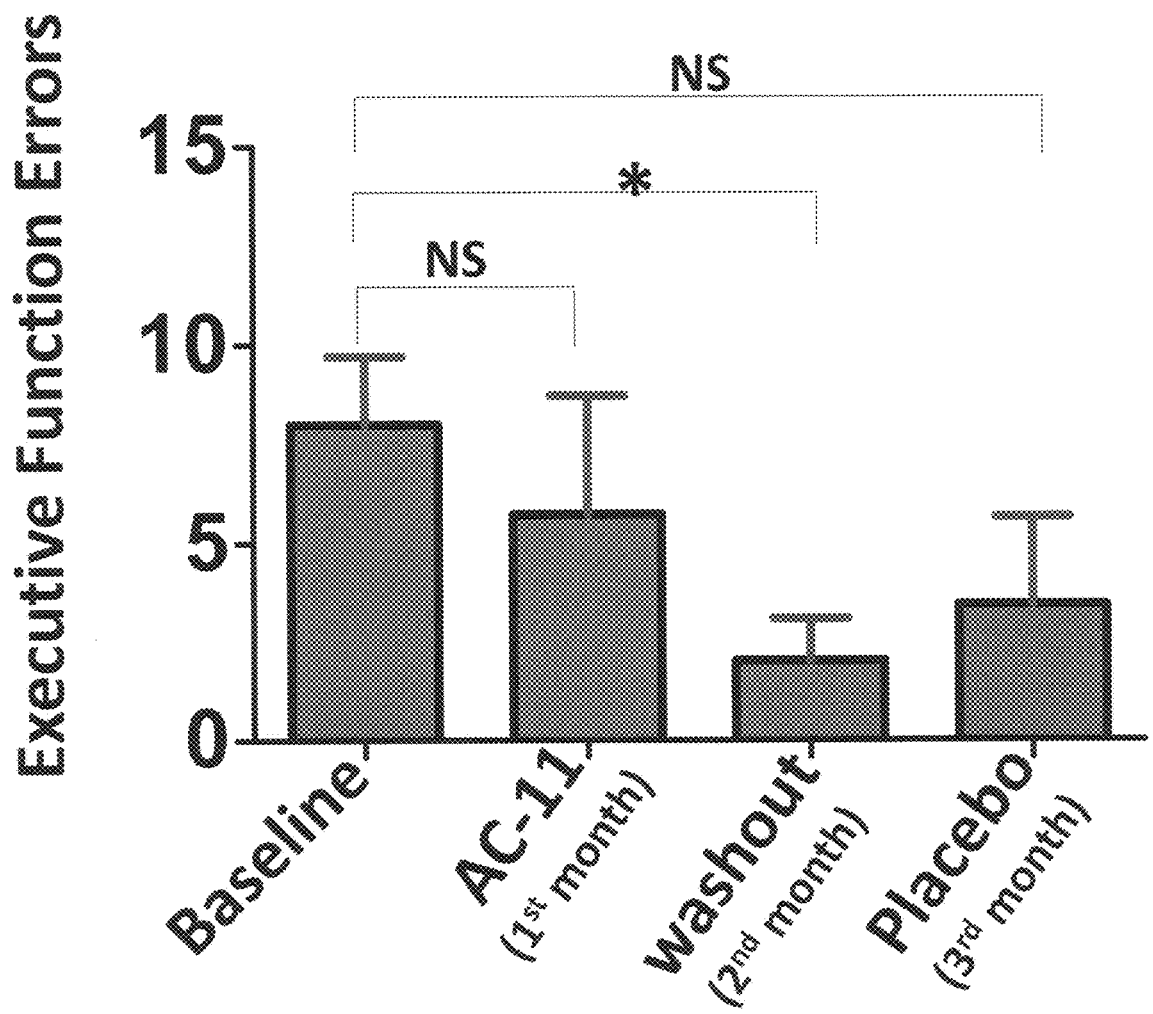
FIG. 5 shows a graph demonstrating that practicing the present invention improves executive function, namely, ability to retain and manipulate visuospatial information.

Executive Function: FIG. 5 reveals that daily oral intake of AC-11® improves executive function among healthy individuals with normal cognitive functions. One month after AC-11® intake began, there was a noticeable improvement in executive function. This improvement continued and even became more pronounced after a 1-month washout period. AC-11® provided both short and long-term benefits to executive function and the long-term benefits are the most prominent. However, placebo intake reversed this trend by creating worse scores among the same participants. It is not clear why the participants would produce poor scores after placebo, but the data suggest that the positive effect of AC-11® on executive function may only last for 2-months. After this 2-month time point, executive function may return to more baseline levels.

FIG. 5: Oral intake of AC-11® improved executive function (e.g., retention and manipulation of visuospatial information). The figure shows quantification of executive function errors for participants at baseline (the beginning of the study). These participants first experienced 1-month of AC-11® by oral intake. Note that their executive function errors did not improve after 1-month of AC-11® intake. Next, the participants experienced a 1-month washout period (rest period). Their executive function errors were significantly reduced and statistically different from baseline. This means that the AC-11® intake had a delayed effect on improving their executive function. This was confirmed by the fact that placebo treatment caused an increase in executive function errors. Bars=mean±S.E.; NS=not statistically significant; *=p<0.05 or statistically significant.

Statistical computations further confirmed the positive effect of AC-11® intake. At 1-month after AC-11® treatment the mean scores were better than that at baseline but did not reach statistical significance (t[10]=1.656, p=0.1287; two-tailed). However, after an additional month (2-month study duration) there was a statistically significant improvement (t[9]=3.712, p=0.0048; two-tailed) in executive function. This indicates that it may take 2-months after the cessation of AC-11® intake to observe a significant improvement in executive function. In contrast, other cognitive domains, such as attention showed improvement as early as 1-month following cessation of AC-11® intake. Statistical computations also showed that executive function may return to baseline levels (t[8]=2.253, p=0.0543; two-tailed) after 3-months. A further indication that AC-11® induced improvement in executive function may only extend out to 2-months.

Figure 6:
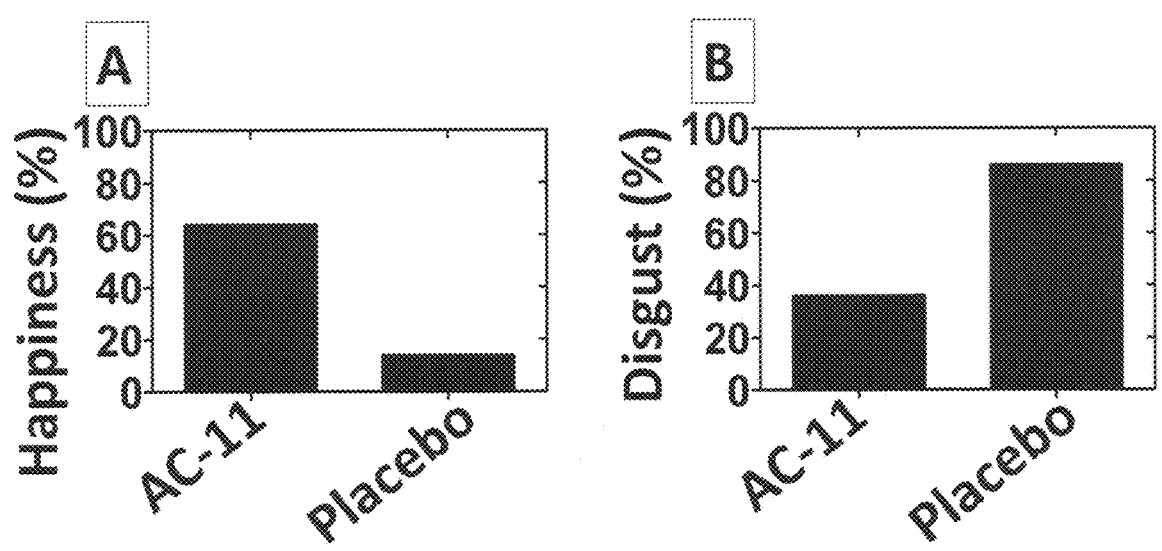
FIG. 6 shows bar graphs demonstrating that practicing the present invention results in improved social cognition.

Social Cognition: FIG. 6 reveals that daily oral intake of AC-11® results in a positive social disposition. FIG. 6A shows that the majority (64%) of participants who consumed AC-11® exhibited social scores that were consistent with a happy disposition. This was confirmed in FIG. 6B, where only a small proportion (36%) of participants who consumed AC-11® exhibited social scores that were consistent with a disgust disposition. In contrast, only 14% of participants who consumed the placebo evidenced social scores that were consistent with a happy disposition. Furthermore, 86% of participants who consumed the placebo demonstrated social scores that were consistent with a disgust disposition.

FIG. 6: Oral intake of AC-11® improved social cognition. Panel A shows the percentage (%) of participants who exhibited a preference towards "happiness" after taking AC-11® or placebo for 1 month. Note that AC-11® treatment resulted in more happy facial interpretations. Panel B shows the percentage (%) of participants who exhibited a preference towards "disgust" after taking AC-11® or placebo for 1 month. AC-11® treatment resulted in less disgust facial interpretations.

Based on the exhaustive study described supra, Applicants have reached the following conclusions.

Daily oral intake of AC-11® was found to improve the cognitive performance of healthy individuals with normal cognition. Given that the participants were healthy and already possess normal cognition, the task of improving their cognition was particularly challenging because they were already operating at a relatively high level (e.g., the ceiling effect). Nonetheless, the results from the study demonstrate that AC-11® intake can significantly improve cognition. AC-11® intake was effective at enhancing cognition in four cognitive domains: attention, executive function, memory and social cognition. The results for attention appear to be more significant and sustained relative to the results from the other domains. For instance, administration of AC-11® improved attention for participants who were initially randomized to receive AC-11® for the first month of the study then placebo for the last month of the study. AC-11® also improved attention for participants who were initially randomized to receive placebo for the first month of the study then AC-11® for the last month of the study. In both scenarios, AC-11® showed statistically significant improvements in attention. Although AC-11® also showed improvements in executive function, memory and social cognition, it is possible that these improvements may be due to the improvement in attention. Primary improvement in attention secondarily enhances a variety of other cognitive functions. Alternatively, AC-11® acts to independently improve performance within each cognitive domain, with attention receiving the greatest impact. In this situation, prolonged use of AC-11® (e.g., additional months of AC-11® intake) or an increase in AC-11® concentration yields improvements in other neurocognitive domains that meet or exceed the improvements in attention.

Cognitive test results at baseline were improved after consuming AC-11®. This demonstrates a gain effect, where the participants gained by taking AC-11®. This gain was evidenced as early as 1-month after AC-11® consumption and could also be observed two and three months later. For instance, attention scores improved after 1-month of AC-11® and this improvement continued out to three month. Given that the study ended after three months, it is possible that this gain effect may have persisted longer. Memory, executive function and social cognition also evidenced gain effects following AC-11® consumption. However, these gain effects were less persistent relative to that of attention. Therefore, consumption of AC-11® may result in long-term improvement in attention but improvements in other cognitive domains require appropriate planning. For instance, improvement in executive function occurs after 2-months of AC-11® consumption, while improvement in memory occurs after 3-months of AC-11® consumption.

Cohort Effect: An important outcome from the research described supra is the fact that the AC-11® group demonstrated cognitive improvement while the placebo group did not. This is suggestive of a cohort effect, where one cohort (group) outperforms another. A cohort effect was most prominent for attention. For instance, the group that received AC-11® consistently showed improved attention across all time points. The group that received placebo failed to exhibit an improvement in attention yet this same group could be improved when they received AC-11®. For memory, only the placebo cohort showed improvement with AC-11® intake. In this cohort, the participants started with placebo consumption then they experienced a washout period followed by AC-11® consumption. It is possible that AC-11® consumption improved their memory scores but it is equally possible that improvements in their memory scores were due to a placebo effect. Support for a placebo effect is the fact that their scores were already improving before AC-11® intake. However, support for an AC-11® effect is the fact that the placebo effect failed to achieve statistical significance while the AC-11® effect achieved statistical significance. With regard to executive function, there was a clear AC-11® induced effect among the AC-11® cohort. These participants received AC-11® then experienced a washout period followed by placebo intake. AC-11® induced an improvement in executive function that started at 1 month and continued to improve after this one month period. Interestingly, consumption of the placebo reversed this positive improvement, an indication that unlike "attention," improvement in executive function is less resilient. Interestingly, AC-11® outperformed the placebo in the area of social cognition across both cohorts. Therefore, a prominent conclusion from the study is that different cohorts can benefit in different ways from AC-11® induced cognitive improvements.

Implications: The results from the exploratory pilot study are supportive of five implications. First, daily oral intake of AC-11® improves cognition among healthy individuals who already have normal cognitive functions. This is evidenced by the improvement in attention scores relative to that at baseline. Therefore, individuals who require a "cognitive boost" before occupational, recreational, educational or social encounters may benefit from daily oral intake of AC-11®.

Second, beneficial effects of AC-11® on specific neurocognitive domains is time dependent. For instance, improvement in attention may occur within 1-month, while improvement in executive function may occur in 2-months and 3-months for memory. With appropriate planning, individuals may consume AC-11® to achieve the desired neurocognitive outcome at the necessary time.

Third, AC-11® induced improvement in attention was significant across cohorts/groups. However, AC-11® induced improvement in other cognitive domains was group dependent. These findings suggest that AC-11® may more directly target the neural substrates that underlie attention. Therefore, consuming AC-11® to improve attention might be a general/global outcome for most individuals. However, improvement in other neurocognitive domains might only be specific to some individuals.

Fourth, daily oral intake of AC-11® may improve social cognition. This is a neurocognitive domain that is rarely assessed yet it is the foundation of normal human social interactions and when perturbed may serve as a marker for a variety of abnormal psychiatric/psychologic conditions (Adolphs, 2009; Cotter et al., 2018). Therefore, individuals may consume AC-11® in order to improve their social cognition.

Fifth, given that daily oral intake of AC-11® improved cognitive performance among individuals who already have normal cognitive function, then it might be possible for AC-11® to improve cognitive function among individuals who suffer with cognitive decline. However, additional studies are need to confirm the results of the present study and to explore whether or not AC-11® would be efficacious among individuals who suffer with cognitive decline.

Applicants have found that a daily dosage of 56 to 700 mg of AC-11® will result in improvement of cognitive function. The dose can be ingested in 2 or more spaced portions of the daily dose. The improvement in cognition is exhibited in as little as one day and up to after 30 or more days. This variation results from differing physiologies of different people. Variations in weight or mass, degree of systemic inflammation, epigenetic activity, genetic mutation and % of fat, among others.

The AC-11® substance can be delivered to the patient in many ways, including in a capsule, by a tablet, a liquid, a syrup, a gel, a transdermal patch, an intranasal spray and/or a suppository.

As such, an invention has been disclosed in terms of a preferred embodiment thereof which fulfills each and every one of the objects of the invention as set forth hereinabove, and provides a new and useful method of enhancing cognition in individuals with at least normal cognition of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

The invention claimed is:

1. A method of enhancing cognition in a human subject exhibiting substantially normal cognition, including the steps of:
   a) administering a first test known as the Folstein Mini-Mental State examination to said subject to determine their level of cognition;
   b) confirming that said subject exhibits normal cognition as evidenced by their achievement of a first score of 20 or greater from taking said first test;
   c) assessing neurocognitive functions of said subject by evaluating said subject employing a second neuropsychological test to obtain a second baseline score;
   d) administering to said subject a substance comprising an aqueous extract of an *Uncaria* species comprising *Uncaria tomentosa* in a pharmaceutically effective amount and for a period of time sufficient to enhance cognition of said subject;
   e) after said period of time has elapsed, re-testing said subject using said second neuropsychological test to determine whether their degree of cognition has become enhanced as compared to their degree of cognition before commencement of administration of said substance;
   f) said method resulting in enhanced cognition being exhibited by said subject as determined by an increased score above said second baseline score.

2. The method of claim 1, wherein said substance is administered orally.

3. The method of claim 1, wherein said pharmaceutically effective amount falls within the range of 56 to 700 mg/day.

4. The method of claim 3, wherein said substance includes a minimum of 8% weight/weight (w/w) carboxy alkyl esters (CAEs).

5. The method of claim 3, wherein said pharmaceutically effective amount comprises about 700 mg/day.

6. The method of claim 5, wherein said substance is administered by taking 350 mg twice per day.

7. The method of claim 1, wherein said substance is administered in a delivery means chosen from the group consisting of a capsule, a tablet, a liquid, a syrup, a gel, a transdermal patch, an intranasal spray, and a suppository.

8. The method of claim 1, wherein said period of time is at least one day.

9. The method of claim 1, wherein said substance is administered orally.

10. The method of claim 1, wherein said substance is administered via a transdermal patch.

11. The method of claim 9, wherein said substance is administered in a delivery means chosen from the group consisting of a capsule, a tablet, a liquid, a syrup, and a gel.

12. The method of claim 1, wherein said first test poses a series of questions to a person and a number of correct answers determines degree of cognition.

13. The method of claim 1, wherein said substance includes a minimum of 8% weight/weight (w/w) carboxy alkyl esters (CAEs).

14. The method of claim 1, wherein said enhanced cognition is in the following categories: attention, memory, executive function, and social cognition.

* * * * *